(12) United States Patent
Brahm

(10) Patent No.: US 9,585,983 B1
(45) Date of Patent: Mar. 7, 2017

(54) WOUND COVERING AND METHOD OF PREPARATION

(71) Applicant: BioDlogics, LLC, Cordova, TN (US)

(72) Inventor: Timothy R. Brahm, Germantown, TN (US)

(73) Assignee: BioDlogics, LLC, Cordova, TN (US)

( * ) Notice: Subject to any disclaimer, the term of this patent is extended or adjusted under 35 U.S.C. 154(b) by 0 days.

(21) Appl. No.: 14/788,847

(22) Filed: Jul. 1, 2015

Related U.S. Application Data

(63) Continuation of application No. 13/650,492, filed on Oct. 12, 2012, now abandoned.

(60) Provisional application No. 61/546,104, filed on Oct. 12, 2011.

(51) Int. Cl.
　　*A61K 35/50*　　(2015.01)
　　*A61K 35/12*　　(2015.01)
　　*A61L 26/00*　　(2006.01)
　　*A61K 35/54*　　(2015.01)

(52) U.S. Cl.
　　CPC ............ *A61L 26/009* (2013.01); *A61K 35/50* (2013.01); *A61K 35/54* (2013.01); *A61L 26/0057* (2013.01)

(58) Field of Classification Search
　　CPC ..... A61K 35/50; A61K 35/12; A61L 27/3604; A61L 2430/40; A61L 2430/34
　　See application file for complete search history.

(56) References Cited

U.S. PATENT DOCUMENTS

| | | | |
|---|---|---|---|
| 4,120,649 A | 10/1978 | Schechter | |
| 4,361,552 A | 11/1982 | Baur, Jr. | |
| 4,674,488 A | 6/1987 | Campbell | |
| 4,894,063 A | 1/1990 | Nashef | |
| 5,607,590 A | 3/1997 | Shimizu | |
| 5,618,312 A | 4/1997 | Yui | |
| 6,152,142 A * | 11/2000 | Tseng | A01N 1/02 128/898 |
| 6,254,637 B1 | 7/2001 | Lee | |
| 6,326,019 B1 | 12/2001 | Tseng | |
| 7,494,802 B2 * | 2/2009 | Tseng | A61F 9/0017 424/424 |
| 2001/0053839 A1 | 12/2001 | Noishiki | |
| 2003/0187515 A1 * | 10/2003 | Hariri | A61K 35/50 623/23.72 |
| 2003/0225355 A1 | 12/2003 | Butler | |
| 2004/0048796 A1 | 3/2004 | Hariri | |
| 2007/0031471 A1 | 2/2007 | Peyman | |
| 2007/0038298 A1 | 2/2007 | Sulner | |
| 2008/0044848 A1 | 2/2008 | Heidaran | |
| 2008/0046095 A1 | 2/2008 | Daniel | |
| 2008/0131522 A1 | 6/2008 | Liu | |
| 2008/0193554 A1 | 8/2008 | Dua | |
| 2008/0274184 A1 | 11/2008 | Hunt | |
| 2009/0208551 A1 | 8/2009 | Kim | |
| 2010/0104539 A1 * | 4/2010 | Daniel | A61L 27/3604 424/93.7 |
| 2010/0106233 A1 | 4/2010 | Deeken | |
| 2011/0129520 A1 | 6/2011 | Bogdansky | |
| 2011/0189301 A1 | 8/2011 | Yang | |
| 2012/0009644 A1 | 1/2012 | Goldstein | |
| 2012/0009679 A1 | 1/2012 | Walsh | |
| 2012/0078378 A1 | 3/2012 | Spencer | |
| 2012/0083900 A1 | 4/2012 | Wilkins | |

FOREIGN PATENT DOCUMENTS

| | | | |
|---|---|---|---|
| EP | 0781564 A2 | 7/1997 | |
| WO | 9310722 A2 | 6/1993 | |
| WO | 2009044408 A1 | 4/2009 | |
| WO | WO 2009044408 A1 * | 4/2009 | ............. A61K 35/50 |
| WO | WO 2009132186 A1 * | 10/2009 | ............. A61K 35/48 |
| WO | 2012003377 A2 | 1/2012 | |
| WO | 2012112417 A2 | 8/2012 | |
| WO | 2012112441 A1 | 8/2012 | |

OTHER PUBLICATIONS

Pardo, M.E.M., et al., "Clinical Application of Amniotic Membranes on a Patient with Epidermolysis Bullosa", Annals of Transplantation, vol. 4, No. 3-4, (1999), pp. 68-73.

Rao, T.V., et al., "Use of Dry Human and Bovine Amnion as a Biological Dressing", Arch Surg, vol. 116 (Jul. 1981), pp. 891-896.

\* cited by examiner

*Primary Examiner* — Frederick Krass
*Assistant Examiner* — Tracy Liu
(74) *Attorney, Agent, or Firm* — Brinks Gilson & Lione

(57) ABSTRACT

A wound covering fabricated from amniotic, chorionic, or intact amniotic and chorionic membranes obtained from human birth tissue is provided. Methods of processing a membrane to form a wound covering are provided. Methods of treating a wound or surgical incision are also provided.

12 Claims, 16 Drawing Sheets

WOUND COVERING AND METHOD OF PREPARATION

CROSS-REFERENCE TO RELATED APPLICATIONS

The present application is a continuation of U.S. application Ser. No. 13/650,492 filed Oct. 12, 2012, which claims the benefit of U.S. provisional application No. 61/546,104 filed Oct. 12, 2011, the contents of which are each incorporated herein by reference in their entirety.

FIELD OF THE INVENTION

The present invention is directed to the field of wound coverings, and, more particularly, to wound coverings composed of amniotic, chorionic, or intact amniotic and chorionic membranes recovered aseptically from human birth tissue, as well as methods of processing the same to prepare a wound covering and methods of using the same to treat a wound or surgical incision.

BACKGROUND OF THE INVENTION

Human placental tissue has been used in various surgical procedures, including skin transplantation and ocular surface disorders, for over a century. The tissue has been shown to provide good wound protection, prevent surgical adhesions, reduce pain, reduce wound dehydration, and provide anti-inflammatory and anti-microbial effects.

The placenta is a fetomaternal organ consisting of a placental globe, umbilical cord, associated membranes (chorionic membrane and amniotic membrane), other gelatins, fluids, cells and extracellular material. The chorionic membrane and the amniotic membrane are attached by loose connective tissue and make up the placental sac. The innermost membrane of the placental sac is the amniotic membrane, which comes into contact with the amniotic fluid that surrounds the fetus. The amniotic membrane is avascular and lined by simple columnar epithelium overlying a basal membrane. The chorionic membrane is the outermost layer of the sac and is heavily cellularized. The placental membranes have an abundant source of collagen that provides an extracellular matrix to act as a natural scaffold for cellular attachment in the body. Collagen provides a structural tissue matrix that facilitates, among other things, cell migration and proliferation in vivo.

Various manufacturing processes have also been employed to create wound coverings composed of amniotic membrane, chorionic membrane, or intact amniotic and chorionic membranes recovered aseptically from human birth tissue after elective Cesarean surgery. There remains a need, however, for membranes that are uniquely processed to enhance the tissue's physical properties and to provide a material that can be stored for easy use.

SUMMARY OF THE INVENTION

The present invention is generally directed to a wound covering, and processes for producing the wound covering. The wound covering of the present invention has unique properties that prevent fibrous scar formation when implanted postoperatively after a variety of surgical procedures. The wound covering can be cut into a variety of sizes for virtually any post-operative surgical procedure where anti-scar formation and/or advanced healing is desired (e.g., spine surgeries, knee surgeries, shoulder surgeries, OB/GYN procedures, urological procedures, plastic surgeries, trauma-related cases, cardiovascular procedures, brain/neurological procedures, sport injury surgeries, soft tissue repair, burn and wound care), or in any other procedure where a wound covering or an anti-adhesion barrier is desirable. The wound covering may also be placed on other areas of the body that have sustained damage but have not been subjected to surgical intervention.

According to one aspect, a wound covering is provided that includes at least one cross-linked amniotic membrane, or at least one cross-linked chorionic membrane, or at least one cross-linked amniotic membrane and at least one cross-linked chorionic membrane. The membrane(s) is/are cross-linked with a cross-linking solution comprising from about 0.05% to about 3% glutaraldehyde. The cross-linked membrane(s) is/are treated with at least one alcohol composition followed by terminal sterilization to form a wound covering. The alcohol composition comprises from about 90% to about 99% ethanol. Terminal sterilization is carried out via gamma irradiation or electron beam irradiation.

According to another aspect, a method of preparing a membrane for a wound covering is provided. The method includes the steps of:

(a) obtaining amniotic membrane, chorionic membrane, or both amniotic and chorionic membrane from a seronegative, healthy human via Cesarean section or vaginal delivery;

(b) immersing the membrane in a basin containing a sterile saline solution;

(c) agitating the basin to liberate excess blood and fluids from the membrane;

(d) rinsing the membrane with a sterile saline solution;

(e) covering the membrane with a substrate on both the fetal membrane side and the maternal membrane side;

(f) optionally, immersing the membrane in a preservative solution for a period of up to about 20 minutes, wherein the preservative solution comprises from about 0.05% to about 3% glutaraldehyde, an alcohol composition or a combination thereof;

(g) optionally, rinsing the membrane with a sterile saline solution;

(h) optionally, soaking the membrane in a sterile saline solution;

(i) immersing the membrane in an alcohol composition for a period of from about 24 hours to about 384 hours;

(j) removing the substrate from both the fetal membrane side and the maternal membrane side;

(k) spreading the membrane on a flat, dry and sterile surface;

(l) allowing the membrane to air dry completely at ambient temperature for a period of up to three hours;

(m) cutting the membrane to a predetermined size; and (n) placing the fetal side of the membrane directly onto a pre-cut substrate to form a wound covering.

The method of preparing a membrane for a wound covering may further include the steps of packaging the wound covering in a dry state and terminally sterilizing the packaged wound covering using irradiation. According to one embodiment, the method may further include the step of removing the chorionic membrane via blunt dissection and discarding the chorionic membrane. According to another embodiment, the method may further include the step of placing the membrane in sterile saline solution for a period of up to about five days between steps (a) and (b). In such an embodiment, the sterile saline solution includes from about 0.9% to about 20% NaCl. According to one embodiment, the sterile saline solution in step (b) may include from about 0.9% to about 20% NaCl. According to one embodiment, the sterile saline solution in steps (d) and (g) may also include from about 0.9% to about 20% NaCl. According to one embodiment, the rinse steps (d) and (g) are conducted for a maximum time period of five minutes. According to one embodiment, the sterile saline solution in step (h) comprises from about 0.9% to about 20% NaCl, and the soak in step (h) is conducted for a maximum period of about 35 minutes. According to one embodiment, the preservative solution comprises 0.1% glutaraldehyde. According to one embodiment, the alcohol composition in steps (f) and (i) each include from about 90% to about 99% ethanol. According to another embodiment, the alcohol composition in steps (f) and (i) each include 95.5% ethanol. According to one embodiment, the method further includes the step of treating the membrane with hydrogen peroxide between steps (a) and (b). According to such an embodiment, the step of treating the membrane further includes the steps of:

(a) rinsing the membrane with about 120 ml of sterile isotonic solution per gram of tissue for a time period of up to about ten minutes;

(b) treating the membrane with about 60 ml of hydrogen peroxide per gram of tissue for a time period of up to about ten minutes; and (c) rinsing the membrane with about 120 ml of sterile isotonic solution per gram of tissue for a time period of up to about ten minutes.

According to another aspect, a wound covering is provided that is produced by the aforementioned method. According to one embodiment, glutaraldehyde residual levels determined by gas chromatography are not detected at the corresponding minimum reporting limit. According to one embodiment, the ethanol residual levels determined by gas chromatography are not detected at the corresponding minimum report limit.

According to another aspect, a method of treating a wound is provided. The method of treating a wound includes the steps of preparing a wound covering as provided herein and placing the wound covering on or around a wound. According to one embodiment, the wound includes a diabetic ulcer, decubitus ulcer, venous leg ulcer, arterial leg ulcer, cutaneous ulcer, or a wound arising on or around a soft tissue, nerve, organ, vascular tissue, muscle, spinal cord, bone, oral cavity, ocular surface, or a combination thereof. According to one embodiment, the method further includes the step of hydrating the wound covering at an application site. According to one embodiment, the wound covering is employed for post-surgical adhesion prevention.

DETAILED DESCRIPTION OF THE INVENTION

Figure 1:
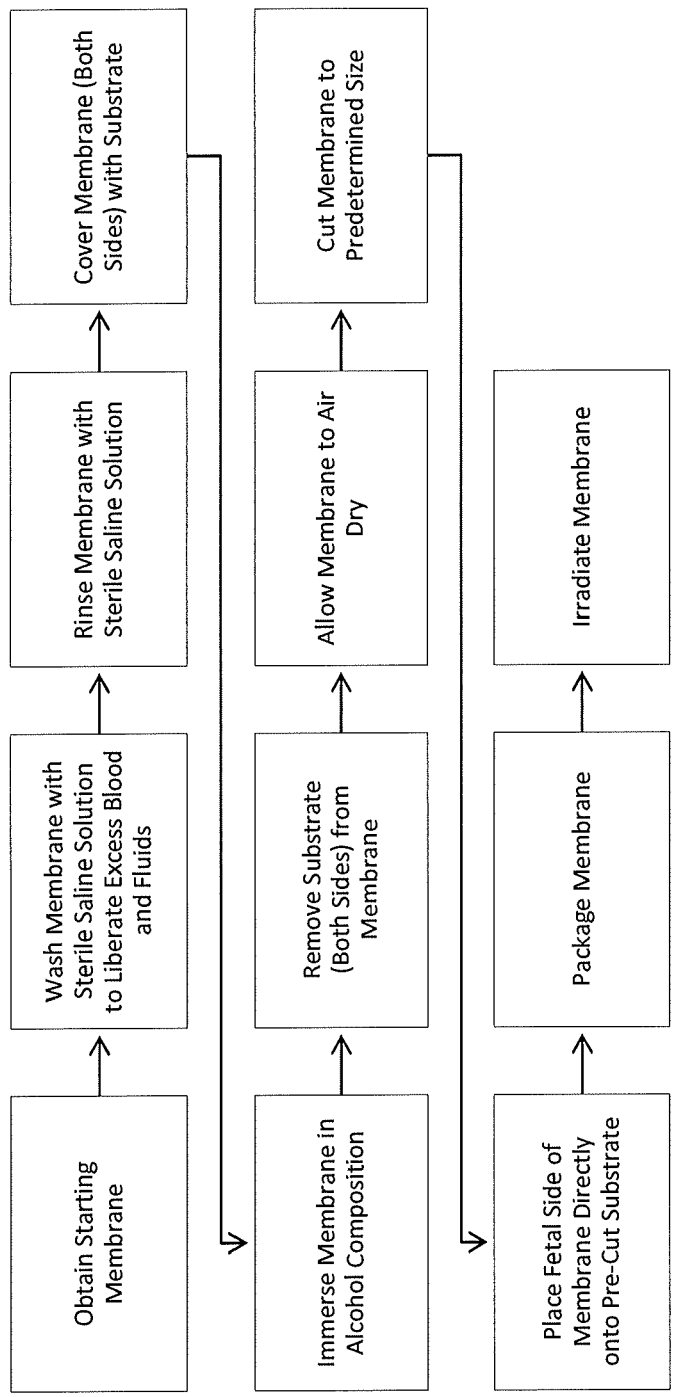
FIG. 1 illustrates a method of preparing a wound covering according to one embodiment.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur. For example, the phrase "optionally soaking the membrane" means that the soaking step may or may not be performed.

The present invention generally relates to a wound covering that is prepared from human birth tissue. As used herein, the term "human birth tissue" includes, but is not limited to, elements of the placental organ such as, for example, the placental globe, umbilical cord, associated membranes (chorionic membrane and amniotic membrane), other gelatins, fluids, cells and extracellular material obtained from a seronegative, healthy human. As used to herein, the term "wound covering" refers to a construct that is applied onto or around an injured area of the body. As used herein, the term "wound" refers to an injured area of the body. Exemplary wounds include incisions, ulcers or other lesions arising from an external force, disease, or surgery.

In particular, the invention relates to the use of amniotic membrane, chorionic membrane, or a combination of amniotic and chorionic membranes obtained from human birth tissue to form a wound covering. In a preferred embodiment, the wound covering provides a sterile structural wound covering that forms a physical barrier to preserve planes of tissue and inhibit adhesion formation, thereby aiding in the healing process. In a preferred embodiment, the wound covering is fully resorbed by the body during the healing process. The invention further relates to methods for aseptically processing intact amnion and chorion membranes to produce a material that may be used to prepare a wound covering.

In one embodiment, the wound covering acts a barrier between the dura and the surrounding soft tissue or paraspinal muscles to reduce fibroblast infiltration into the epidural space where post-operative scar tissue normally forms. By reducing fibroblast infiltration, the wound covering of the present invention: (i) reduces epidural fibrosis at a surgical site; and (ii) acts as a structural barrier to preserve the plane between the dura and the surrounding soft tissue to reduce the tethering of adhesions to the dura or nerve roots. Intact amnion, chorion, or amnion and chorion membranes incorporated in the wound covering reduce both the accumulation of scar tissue and the tenacity of the scar tissue that may form. Thus, the present wound covering reduces the potential for post-operative complications associated with scar tissue formation.

The wound covering can also be utilized outside of normal surgical procedures. For example, the wound covering of the instant invention can be placed on a persistent wound. The wound may arise in a variety of forms including, but not limited to, a burn, diabetic ulcer, decubitus ulcer, venous leg ulcer, arterial leg ulcer, or cutaneous ulcer. The wound covering may also be utilized on any wound arising on or around a soft tissue, nerve, organ, vascular tissue, muscle, spinal cord, bone, oral cavity, ocular surface, or a combination thereof.

The amniotic and chorionic membranes may be utilized alone or in various combinations or layers to form the wound covering. The present disclosure provides methods of preparing a wound covering that includes an amniotic membrane, a chorionic membrane, or both a chorionic and an amniotic membrane. Thus, the term "membrane" refers to an amniotic membrane, a chorionic membrane, or both a chorionic and an amniotic membrane. According to one embodiment, the wound covering includes one or more layers including an amniotic membrane. According to another embodiment, the wound covering includes one or more layers that include a chorionic membrane. According to yet another embodiment, the wound covering includes one or more layers of an amniotic membrane and one or more layers of a chorionic membrane.

According to one embodiment, the wound covering includes at least one cross-linked amniotic membrane, or at least one cross-linked chorionic membrane, or at least one cross-linked amniotic membrane and at least one cross-linked chorionic membrane. In such an embodiment, the membrane(s) is/are cross-linked by treating the membrane(s) with a glutaraldehyde composition. The glutaraldehyde composition includes glutaraldehyde typically in an amount of from about 0.05% to about 3%. The resulting membrane(s) is/are treated with at least one alcohol composition and then terminally sterilized to form a wound covering.

According to one embodiment, the wound covering includes at least one amniotic membrane, or at least one chorionic membrane, or at least one amniotic membrane and at least one chorionic membrane. In such an embodiment, the membrane(s) is/are not cross-linked. The membrane(s) is/are treated with one alcohol composition that include typically from about 90% to about 99% ethanol. The resulting membrane(s) is/are terminally sterilized to form a wound covering.

According to another embodiment, the wound covering includes at least one amniotic membrane, or at least one chorionic membrane, or at least one amniotic membrane and at least one chorionic membrane. In such an embodiment, the membrane(s) is/are not cross-linked. The membrane(s) is/are treated with at least two alcohol compositions that each include typically from about 90% to about 99% ethanol. The resulting membrane(s) is/are terminally sterilized to form a wound covering.

The wound covering as described herein may be of various sizes, thickness, and shapes. The wound covering is preferably of sufficient size and shape to be applied onto or around a wound that is on or in a patient's body. The wound covering thickness may vary depending on application, the type of membrane and the number of membrane layers. Typically, the wound covering is from about 0.02 mm to about 0.35 mm thick.

Potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-I and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental organ, including the placental globe, umbilical cord, associated membranes (chorionic membrane and amniotic membrane), other gelatins, fluids, cells and extracellular matrix can be recovered from a seronegative, healthy human after the newborn is removed. The placental globe, umbilical cord, other gelatins, fluids, cells and extracellular matrix can be removed and discarded.

The membrane giving rise to the wound covering as described herein may be produced by processing human birth tissue according to the steps provided herein. Processing does not change the physical properties of the resulting membrane so as to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

Throughout processing, the orientation of the particular membrane is identified to ensure that in use the correct side of the membrane is placed on the wound. Either the fetal side or the maternal side of the membrane may be used depending upon the specific use or procedure that is being performed.

Figure 2:
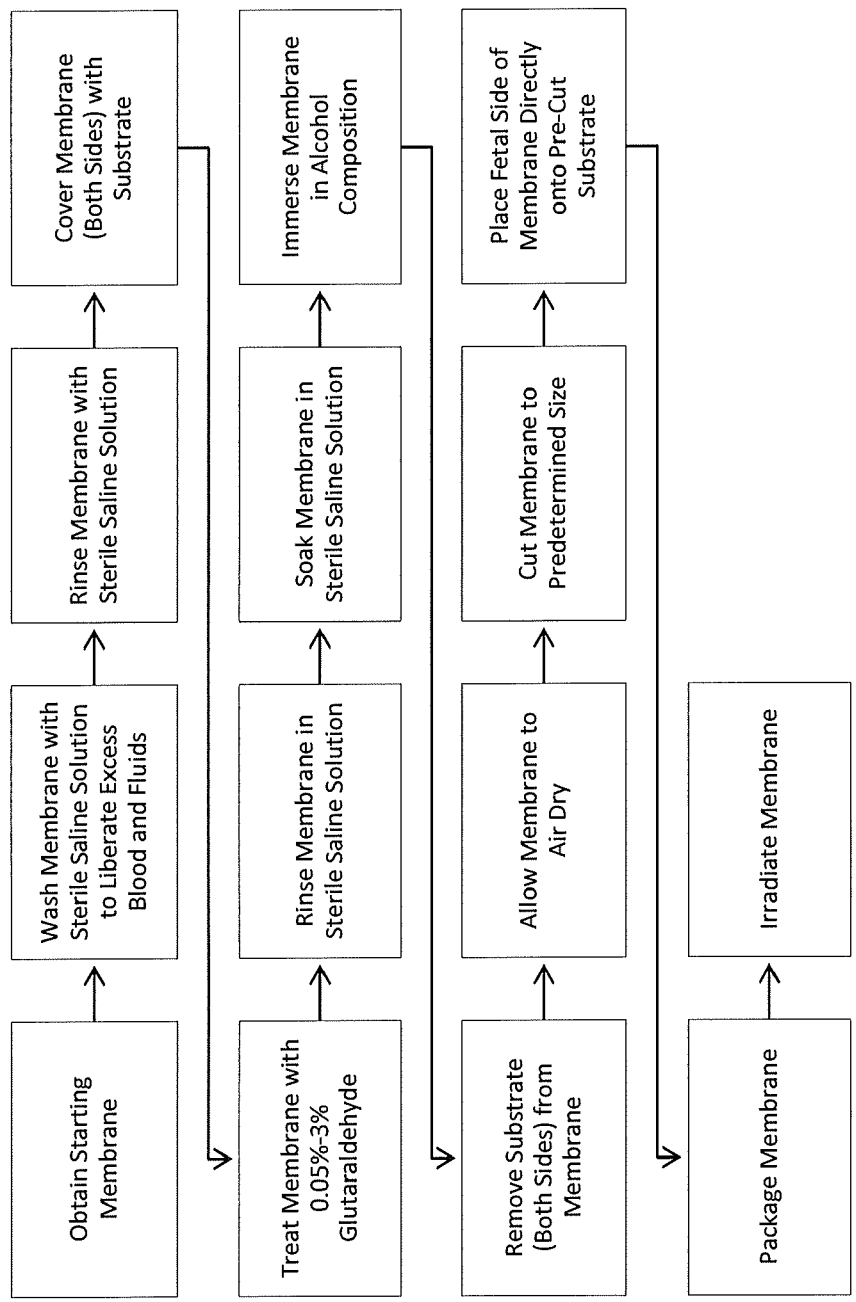
FIG. 2 illustrates a method of preparing a wound covering according to one embodiment.
Figure 3:
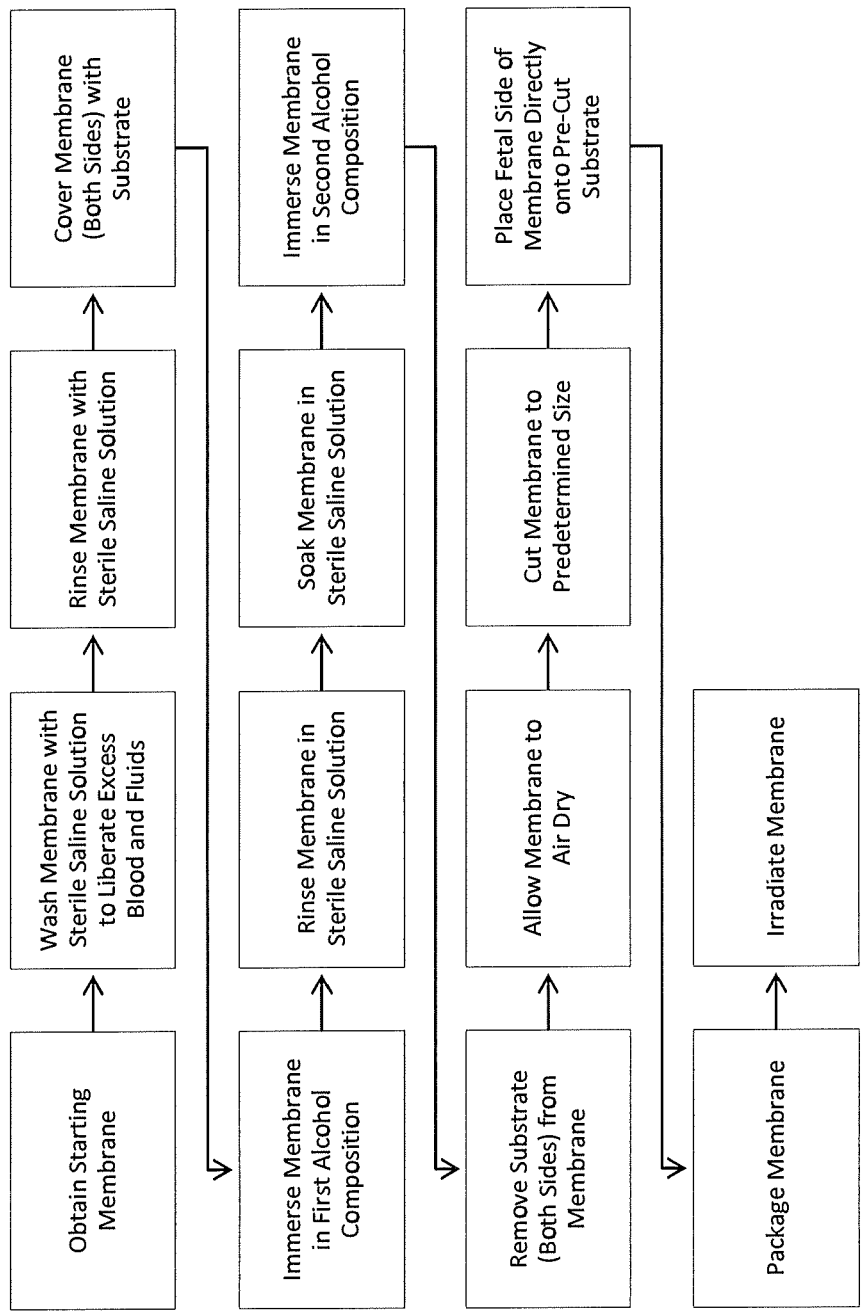
FIG. 3 illustrates a method of preparing a wound covering according to one embodiment.

According to the embodiment as illustrated in FIG. 1, FIG. 2 or FIG. 3, the wound covering is prepared by first obtaining amniotic membrane, chorionic membrane, or both amniotic and chorionic membrane from a seronegative, healthy human via cesarean section or vaginal delivery as described herein. In particular embodiments where only the amniotic membrane is chosen for further processing, the chorionic membrane can be removed by blunt dissection. For example, the chorionic membrane may be removed by applying finger pressure and sliding it off of the amniotic membrane using as little pressure as possible to avoid tearing of the amnion. The chorionic membrane and any excess tissue can be discarded.

The recovered amniotic membrane, chorionic membrane, or both amniotic and chorionic membrane may be initially stored in a sterile saline solution at a temperature between about 1° C. to about 10° C. for a period of up to about 120 hours prior to further processing. According to one embodiment, the sterile saline solution comprises from about 0.09% to about 20% NaCl, preferably 15% NaCl.

Optionally, the membrane may be treated with hydrogen peroxide. Hydrogen peroxide is used as a sterilant and to enhance the solubilization of lipids. Such a treatment process includes the steps of:

(a) rinsing the membrane with 120 ml of sterile isotonic solution per gram of membrane for a period of up to about ten minutes;

(b) treating the membrane with 60 ml of hydrogen peroxide per gram of membrane for a period of up to about ten minutes; and (c) rinsing the membrane with 120 ml of sterile isotonic solution per gram of membrane for a period of up to about ten minutes.

The membrane is then immersed in a basin containing a sterile saline solution. According to one embodiment, the sterile saline solution includes typically from about 0.9% to about 20% NaCl.

Excess blood and fluids may be liberated from the membrane by gently stirring or swirling the fluid in a circular motion in the basin or by placing the basin on a shaker. The membrane can then be rinsed with a sterile saline solution. In one embodiment, the sterile saline solution includes NaCl in a concentration range of about 0.9% to about 20%. In one embodiment, the membrane may be rinsed in bowls or trays of sufficient size to allow the membrane to be spread out to improve the rinse coverage. Sufficient saline solution is utilized to ensure that the membrane is completely immersed. The saline is then decanted into a discard basin.

Multiple saline rinse cycles may be performed. In one embodiment, the membrane is rinsed for two or more separate rinse cycles, with each rinse cycle lasting for a maximum of five minutes. The membrane is covered with a substrate on both the fetal membrane side and the maternal membrane side. Appropriate substrates include, but are not limited to, a sterile mesh or polymer mesh of adequate size and shape for covering each side of the membrane.

According to the embodiment as illustrated in FIG. 2, the membrane is then optionally immersed in a preservative solution for a period of time of typically up to about twenty minutes. The preservative solution includes typically from about 0.05% to about 3% glutaraldehyde and, preferably, about 0.1% glutaraldehyde. The membrane may then be optionally stirred or swirled at a temperature of typically about 22° C. (±1-5° C.). When present, glutaraldehyde leads to collagen cross-linking, which, in turn, leads to a significant increase in the biomechanical strength of the membrane. Additionally, the handling characteristics of the membrane are improved after glutaraldehyde treatment because the membrane is more rigid and does not fold over onto itself. Glutaraldehyde cross-linking also prohibits fast resorption of the membrane by the body after implantation and may be well-suited for guided tissue regeneration due to its ability to prevent cellular infiltration into the surgical site. The glutaraldehyde treatment is preferably performed in a bowl or tray of sufficient size to allow the membrane to spread out in order to maximize exposure of the tissue to the glutaraldehyde solution. Sufficient glutaraldehyde solution should be used to immerse the membrane in the solution. Typically, a minimum of about 400 ml of glutaraldehyde solution is used.

According to the alternative embodiment as illustrated in FIG. 3, the preservative solution may optionally include from about 90% to about 99% ethanol (i.e., in the absence of glutaraldehyde (see FIG. 3—referred to as "first alcohol composition")). In a preferred embodiment, the alcohol composition includes about 95.5% ethanol. A wound covering produced according to the embodiment of FIG. 3 will be resorbed more quickly by the body (as opposed to gluteraldehyde treatment followed by alcohol treatment) and is particularly useful for soft tissue remodeling. This alternative embodiment is particularly useful for treatment of persistent wounds, including diabetic ulcers, decubitus ulcers, venous leg ulcers, arterial leg ulcers and cutaneous ulcers, thereby allowing the graft to be resorbed faster to aid in the healing cascade.

As illustrated in the embodiments of FIGS. 2 and 3, the membrane is then optionally rinsed with a sterile saline solution. Alternatively, the membrane is rinsed multiple times with a sterile saline solution. According to one embodiment, the sterile saline solution includes typically from about 0.9% to about 20% of NaCl. The membrane can then be optionally soaked in a sterile saline solution. According to one embodiment, the sterile saline solution includes typically from about 0.9% to about 20% of NaCl. According to one embodiment, soaking is conducted for a maximum period of about 35 minutes.

As illustrated in each of the embodiments of FIGS. 1, 2, and 3, the membrane is then immersed in an alcohol composition for a period of typically from about 24 hours to about 384 hours. The alcohol composition includes about 90% to about 99% ethanol. In a preferred embodiment, the alcohol composition includes about 95.5% ethanol. Treatment of the membrane within a particular alcohol concentration range for the particular timeframe at this step in the process has yielded unexpected results related to the handling characteristics. One of ordinary skill in the art appreciates the difficulty of handling and manipulating amniotic and chorionic tissue when applied to a surgical site. Specifically, existing amniotic and chorionic grafts are difficult to place over a wound, particularly because these grafts fold back over on themselves ("wrinkling"), rendering proper placement and positioning of the graft at the wound site very challenging. When treated with the aforementioned alcohol composition for the particular timeframe, the resulting wound covering experiences further cross-linking which aids in the handling characteristics of the wound covering. The alcohol-treated membrane does not "wrinkle" and allows for easy placement at the surgical site. Furthermore, the alcohol treatment is multi-functional, providing a means of sterilization, preservation, and chemical dehydration for the graft, in addition to serving as a radioprotectant for the graft prior to terminal irradiation.

The substrate can then be removed from both the fetal membrane side and the maternal membrane side. The alcohol-treated membrane can then be spread on a flat, dry and sterile surface. The membrane is then allowed to air dry completely at ambient temperature for a period of up to typically about three hours. The membrane can then be cut to the desired size, covered with a substrate, and subsequently packaged. The wound covering can be cut into patches of any desired size for a particular application by a rotary type cutting tool. A grooved or similarly indicated cutting board may be used to aid in cutting a straight and correctly sized covering. In another embodiment, the wound covering is cut by free hand using a scalpel and ruler to achieve the desired size. The fetal side of the membrane can then be placed directly onto a pre-cut substrate to form a wound covering. Suitable substrates include, for example, a gauze or synthetic mesh. Preferably, the wound covering is packaged in a dry state. The covering can be removed after the opposing side has been applied to the surgical site. The packaging and covering as disclosed herein can facilitate the handling of the wound covering, namely maintaining and identifying the orientation of the fetal and maternal side of the wound covering for the user. The packaging may also promote storage of the wound covering.

The packaged wound covering can be terminally sterilized using irradiation. In one embodiment, an electron beam irradiation is applied in an amount up to about 45 kGy. The sterilized wound covering may be stored for up to typically about two years from the date of processing. In one embodiment, the wound covering may be stored under proper conditions for as much as about five years following processing. According to a preferred embodiment, the wound covering may be stored under proper conditions for two years following processing. The sterilized wound covering may be stored in any container suitable for long-term storage. Preferably, the sterilized wound covering is stored in a sterile double peel-pouch package.

A method of treating a wound is also provided. According to one embodiment, the wound covering is prepared according to one of the methods as provided herein. The wound covering is then placed on or around a wound, including a surgical site. In one embodiment, the wound includes, but is not limited to, at least one diabetic ulcer, decubitus ulcer, venous leg ulcer, arterial leg ulcer, or cutaneous ulcer. In another embodiment, the wound covering may be used, for example, in surgical procedures including, but not limited to, spine surgeries, knee surgeries, shoulder surgeries, OB/GYN procedures, urological procedures, plastic surgeries, trauma-related cases, cardiovascular procedures, brain/neurological procedures, sport injury surgeries, soft tissue repair, burn and wound care, or in any other procedure where a wound covering or an anti-adhesion barrier is desirable.

In cases where fixation of the wound covering is not required (spine, OB/GYN, general surgery, etc.), the wound covering can be simply placed in the surgical site and held in place by the patient's musculature and skin throughout the recovery process. In an alternative embodiment, sutures or staples may be required to hold the wound covering in place. The wound covering may be hydrated at the application site during treatment.

The wound covering can also be used to cover an implant (metal or biomaterial fixation or support devices) to give the implant anti-adhesion properties. If desired, the membrane may be treated to provide for the delivery of a variety of antibiotics, anti-inflammatory agents, growth factors and/or other specialized proteins or small molecules. In addition, the membrane may be combined with a substrate (sterile gauze, sterile polymer material or other tissue or biomaterial) to increase the strength of the wound covering dressing for sutures or to increase the longevity of an implant. In other embodiments, the membrane can be solubilized or ground up into a powder, gel or liquid and sprayed or poured on the device or tissue implant to prevent tissue adhesion.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

EXAMPLE 1

The wound covering of the present invention has particular utility in dental applications, e.g., periodontal surgery, periodontal ligament reattachment, gingival recession recovery, connective tissue grafting, sinus lifts, socket preservation/augmentation, buccal defect treatment and ridge augmentation. The invention encompasses the use of the wound covering of the present invention to promote enhanced therapeutic utility and enhanced clinical parameters which include, but are not limited to, probing pocket depth, probing attachment depth, bone quality classification (density/volume) and gingival pocket recession.

The following example demonstrates one method of using a wound covering for application at a socket augmentation site.

The wound covering was prepared according to the method of FIG. 2. Human birth tissue was obtained from a seronegative healthy mother via Cesarean section. To maximize the overall quality of the donated tissue, a recovery technician was present in the operating room during the donor's Cesarean section to assist the physician with recovery, treatment and handling of the birth tissue. The donor was surgically prepped and draped per AORN standards prior to the Cesarean section procedure. The recovery technician prepared the recovery site by establishing a sterile field on a back table in the operating room. Following delivery of the baby, the physician's assistant placed the human birth tissue en-bloc into a sterile basin. Maintaining sterility, the basin was transferred to the recovery technician onto the sterile field. Beginning at the amnion/chorion membrane surgical incision site, the recovery technician used blunt dissection to separate the chorionic membrane from the amniotic membrane, using care not to tear the amniotic tissue. The recovery technician then removed the amniotic membrane from the placental face until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with sterile saline to remove any blood or debris.

After thorough rinsing, the amniotic membrane was transferred into a sterile bag and swab cultures were performed. Approximately 300 ml of transport solution (15% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed. The plastic transport container was placed in a qualified shipping container with an appropriate amount of wet ice to maintain refrigerated temperatures. The validated box arrived at the processing facility approximately one hour following recovery and was immediately placed in refrigerated temperatures (1-10° C.) and inspected per standard operating procedures.

Processing was performed on a sterile field using aseptic technique in a validated cleanroom at the processing facility. All manufacturing steps were recorded concurrently by a circulating technician on a designated processing record. The amniotic membrane was removed from the plastic transport container and outer bag. The inner bag containing the amniotic membrane was aseptically passed onto a sterile field. The amniotic membrane was placed maternal side up onto a sterile cutting board. The membrane was inspected for any damage or debris. Any stringy ends were cut away. Keeping the membrane flat on the sterile cutting board, the amnion was rinsed with a sterile saline solution (0.9% NaCl). The maternal side of the membrane was covered with sterile mesh, allowing the mesh to slightly overlap the membrane. The membrane was gently lifted, positioned fetal side up, and placed back on the sterile cutting board, using caution to not disturb the mesh/amnion interface. The fetal side of the membrane was rinsed with a sterile saline solution (0.9% NaCl). Then, the fetal side of the membrane was covered with sterile mesh, allowing the mesh to slightly overlap the membrane. The mesh/membrane/mesh was transferred into a sterile basin, maternal side down, unfolded and flat, using caution not to disturb the mesh/amnion interface. 2 L of a 0.1% glutaraldehyde solution was poured into the sterile pan to fully immerse the amnion/mesh. The sterile pan was covered and transferred onto a sterilely draped orbital shaker programmed with the following settings: 70±10 rpm and 15±1 minutes. Once the cycle was completed, the covered sterile basin was aseptically transferred back onto the sterile field. The glutaraldehyde solution was carefully poured off, using caution not to disturb the mesh/membrane/mesh interface. Approximately 250 ml of sterile saline solution (0.9% NaCl) was added to the sterile basin to thoroughly rinse the pan/mesh/membrane. The 0.9% NaCl was carefully poured off, using caution not to disturb the mesh/membrane/mesh interface. 2 L of sterile saline solution (0.9% NaCl) was added to the sterile basin. The sterile basin was covered and transferred onto a sterilely draped orbital shaker programmed with the following settings: 70±10 rpm and 30±1 minutes. Once the cycle was completed, the covered sterile basin was aseptically transferred back onto the sterile field. The sterile saline solution was carefully poured off, using caution not to disturb the mesh/membrane/mesh interface. 1 L of 95.5% ethanol solution was added to the sterile basin, fully immersing the mesh/membrane/mesh interface and the basin was re-covered. The sterile basin was placed inside a sterile bag and transferred to a quarantine refrigerator. The mesh/membrane/mesh interface remained in the 1 L of 95.5% ethanol solution for 189.6 hours.

A sterile field was established in a validated cleanroom at the processing facility. All manufacturing steps were recorded concurrently by a circulating technician on a designated processing record. The sterile bag containing the sterile basin was removed from the quarantine refrigerator. The sterile basin was removed from the sterile bag and aseptically transferred to the sterile work area in the cleanroom. The mesh/membrane/mesh interface was removed from the 95.5% ethanol solution and placed maternal side down on a sterile cutting board. The mesh was removed from the fetal side of the membrane. The membrane/mesh was carefully flipped and the mesh was removed from the maternal side of the membrane. The membrane was repositioned onto the cutting board in a completely flat position. The membrane was allowed to dry for seven (7) minutes. Using a rotary cutting blade, the membrane was sectioned into product sizes, in accordance with the processing plan. The dry membrane grafts were carefully loosened from the cutting board and placed onto pre-cut sections of mesh with the maternal side of each membrane graft orienting up and the fetal side to the mesh. Each individual tissue patch was packaged into a sterile foil inner pouch using aseptic technique. Using an AccuSeal 540Plus sealer, each foil pouch was sealed inside a Tyvek pouch following standard operating procedures. Each Tyvek pouch was assigned and labeled with a tissue identification number, designed to ensure the traceability of tissue from receipt through clinical use, transfer or destruction. Each unit was terminally sterilized via E Beam irradiation at 27.1-28.5 kGy.

Figure 4:
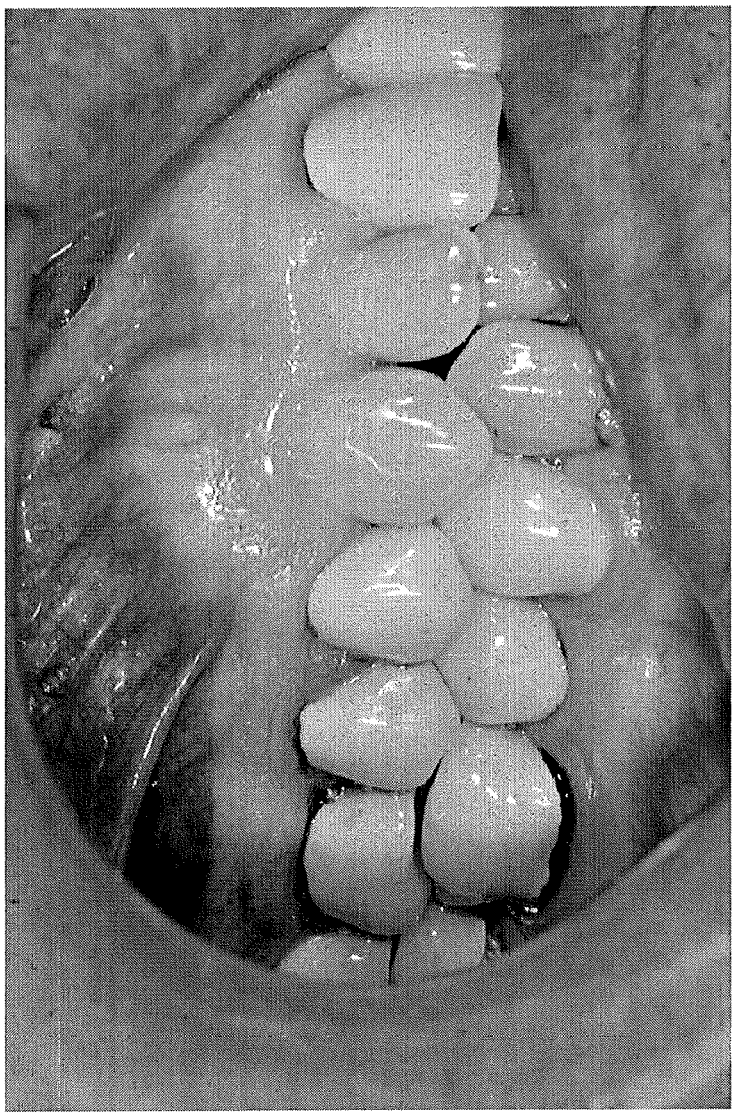
FIG. 4 provides a photo of a dental shallow pocket formation prior to treatment with a wound covering according to one embodiment.

The patient was a 43-year-old female referred by a general dentist to a periodontist for extraction of #4 tooth (Universal Tooth Numbering System) and possible replacement with implant. The clinical findings included a shallow pocket formation (−4 mm or less throughout), recurrent decay for #4 buccal and advanced caries for #4 tooth, in addition to the presence of a crown on #4 tooth splinted with #5 tooth. The individual tooth prognosis for tooth #4 was hopeless because the tooth structure was inadequate to restore (FIG. 4).

Figure 5:
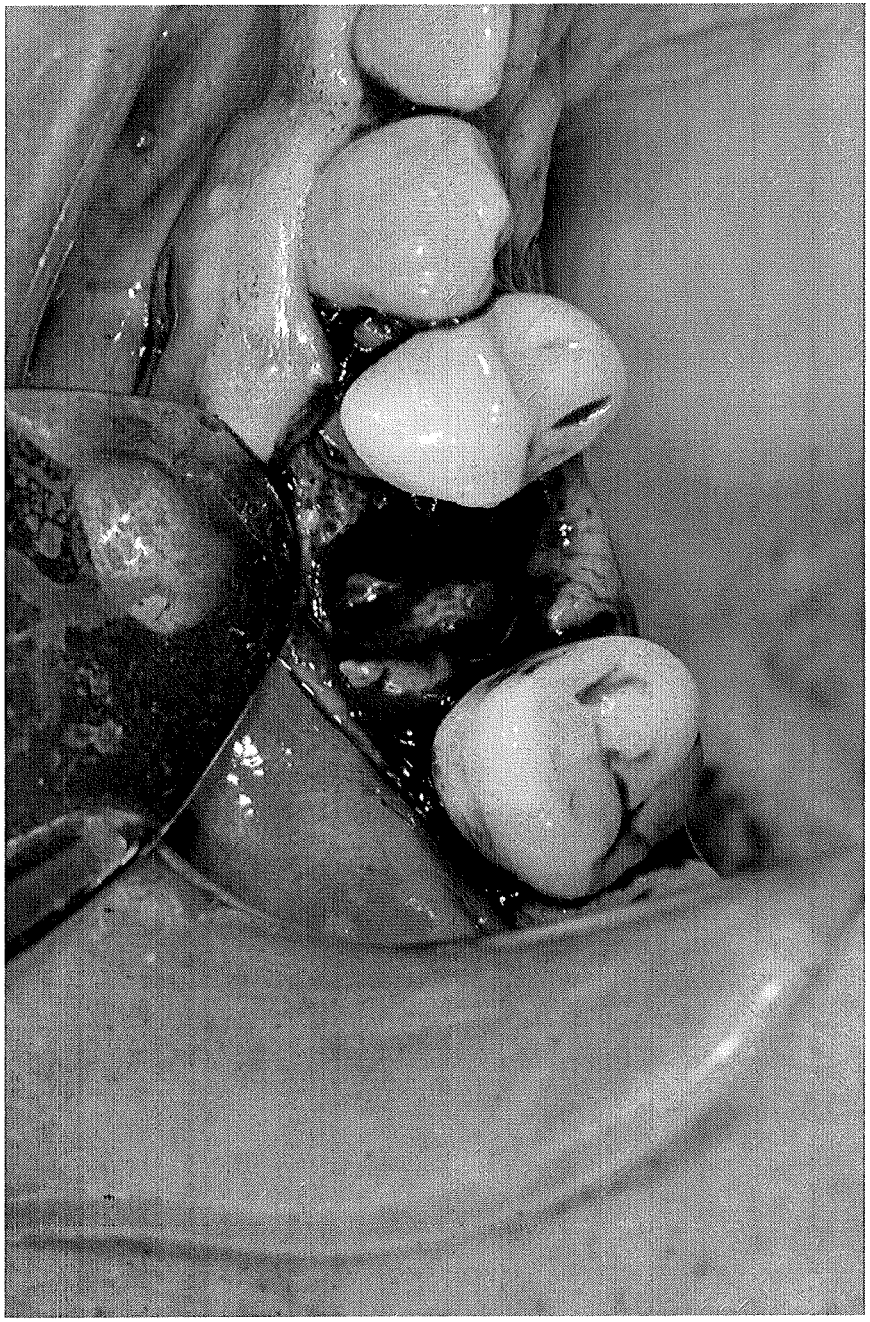
FIG. 5 provides a photo of the dental shallow pocket of FIG. 4 following socket curette and irrigation but prior to treatment with a wound covering according to one embodiment.

Extraction of tooth #4 was performed according to the following method. Access was achieved through full thickness flaps on the buccal and lingual of the #3 and #5 area. The #4 tooth was sectioned horizontally followed by crown removal. The bone was removed from the distal-mesial direction from the internal socket surface to allow access for an elevator. Tooth removal was achieved using forceps, elevators and curettes. Following socket curette and irrigation, the bridge was sectioned between #4 and #5 and the surfaces of the remaining restorations smoothed and polished (FIG. 5).

Figure 6:
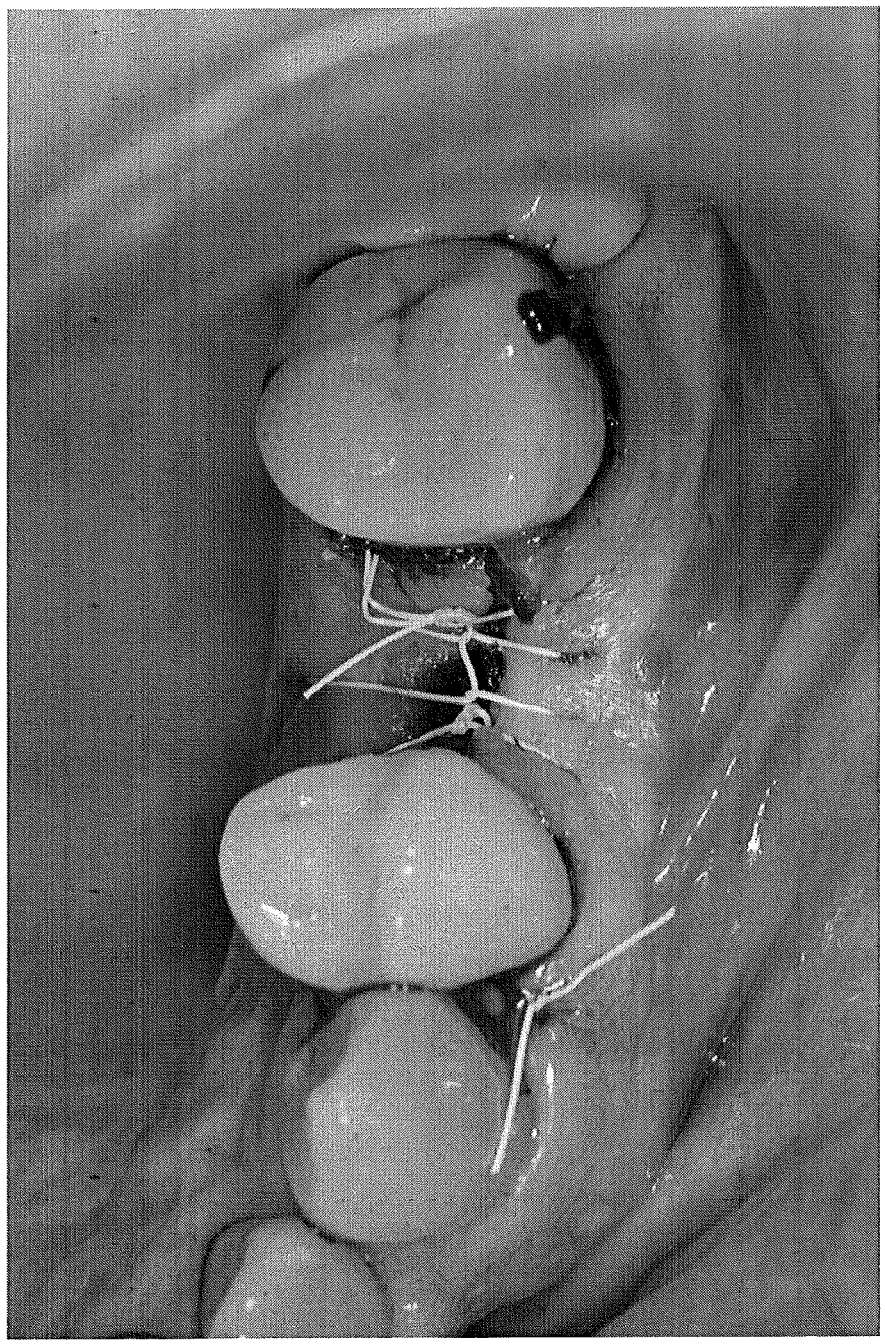
FIG. 6 provides a photo showing one view of the dental shallow pocket of FIG. 4 following wound covering application.
Figure 7:
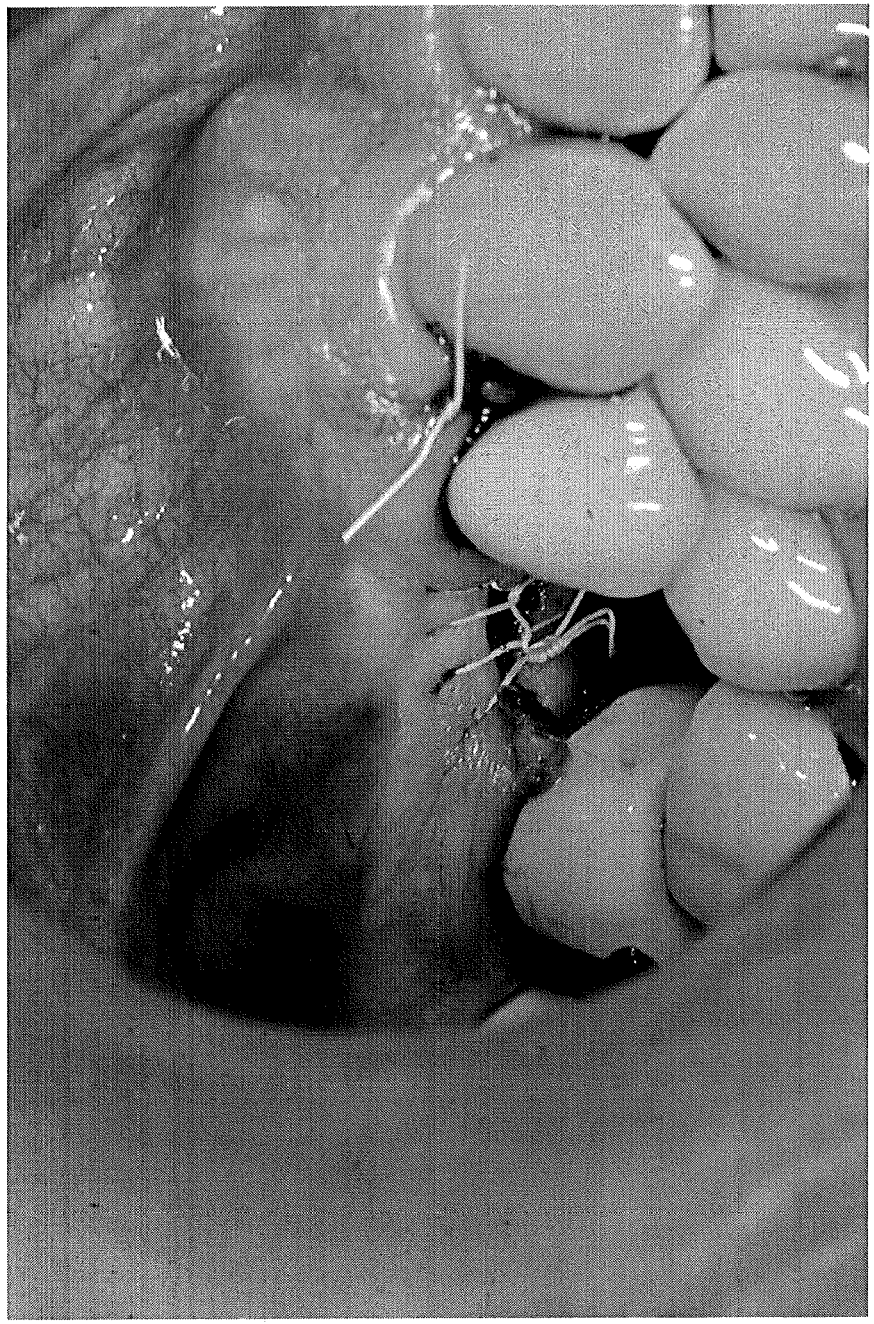
FIG. 7 provides a photo showing another view of the dental shallow pocket of FIG. 4 following wound covering application.

A mineralized freeze-dried bone allograft (FDBA), MinerOss®, was applied to the #4 site, followed by application of the wound covering measuring 1.5 cm×2 cm. Flap closure was obtained in the #4 area, where a slight opening remained (approximately 3 mm) between the buccal and palatal flaps. The wound was closed by interrupted suturing with chromic gut (5-0) (FIGS. 6 and 7).

Figure 8:
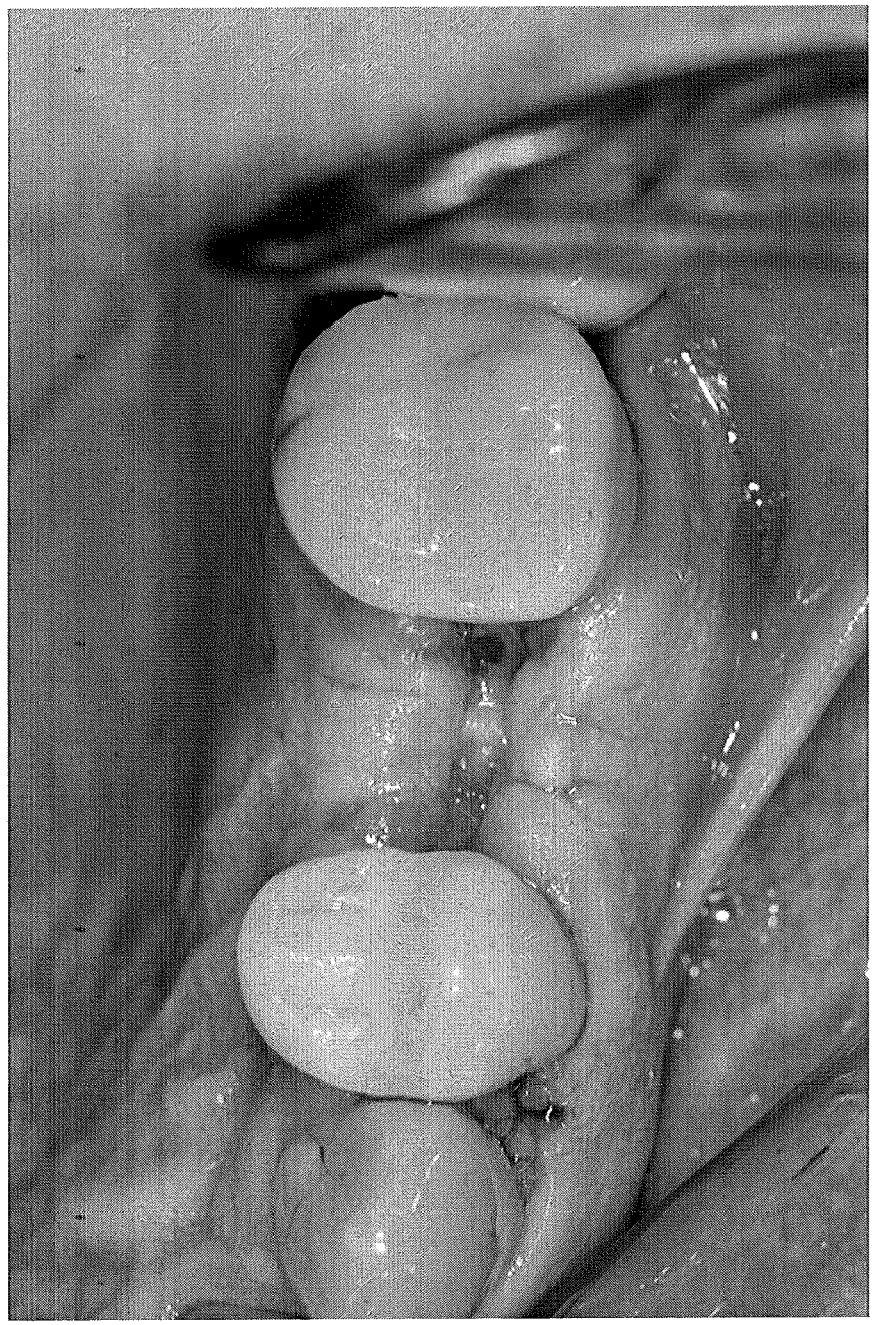
FIG. 8 provides a photo of the dental shallow pocket of FIG. 4 two weeks after wound covering application and after suture removal.
Figure 9:
FIG. 9 provides a photo of a dental extraction site one week after application of two wound coverings at the site.
Figure 10:
FIG. 10 provides a photo of a dental extraction site one week after application of two wound coverings at the site.
Figure 11:
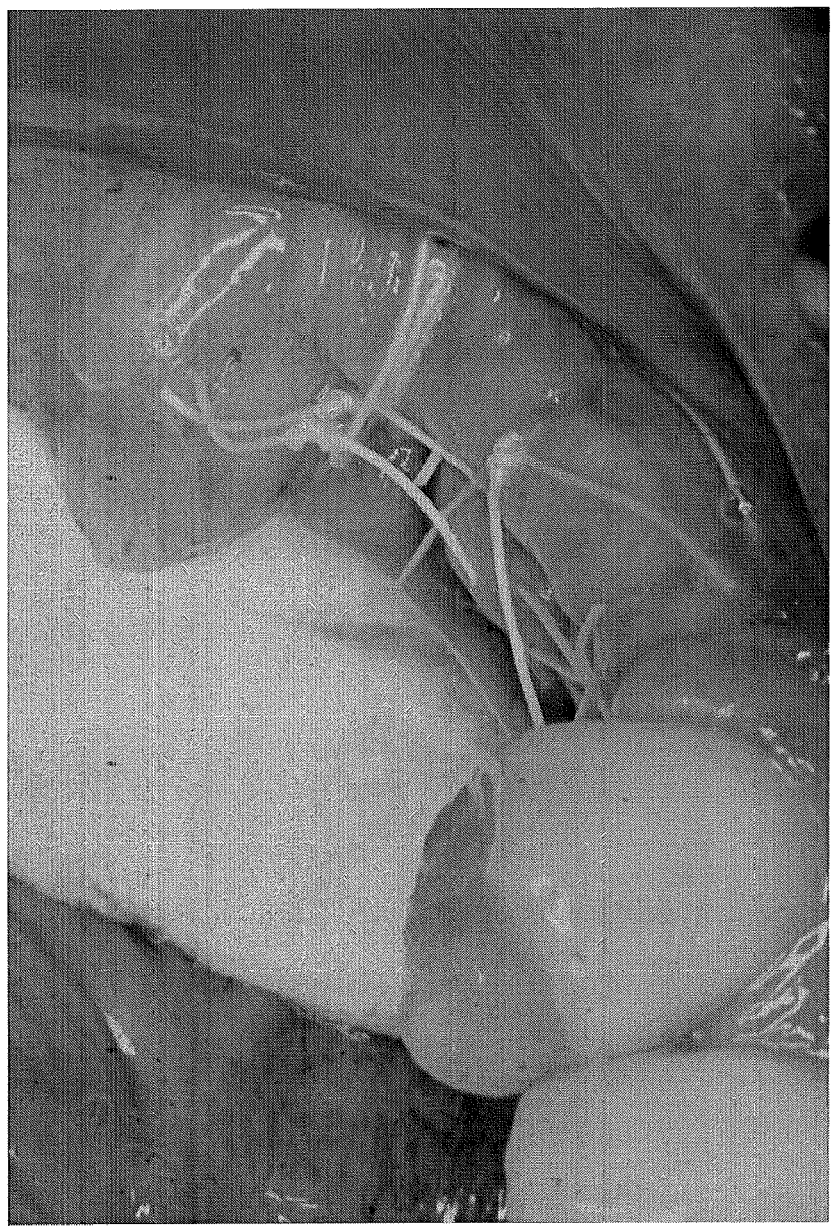
FIG. 11 provides a photo of a dental extraction site two weeks after application of two wound coverings at the site.
Figure 12:
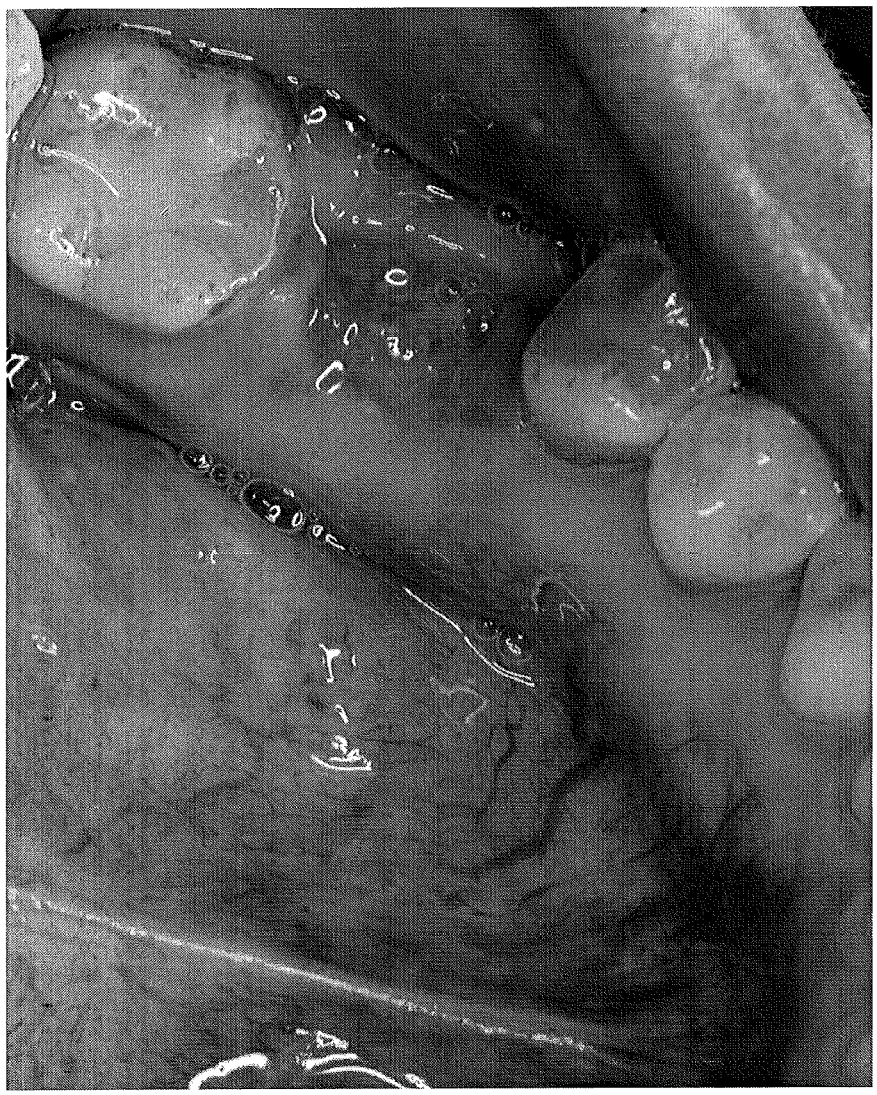
FIG. 12 provides a photo of a dental extraction site four weeks after application of two wound coverings at the site.

A two-week postoperative visit indicated that the patient had experienced no discomfort, tenderness, intraoral swelling, extraoral swelling, difficulty eating/chewing, bleeding when brushing/flossing or temperature sensitivity to the affected area. The objective findings included wound healing in a moderate stage to advanced stage with excellent postoperative progress (FIG. 8).

EXAMPLE 2

The following example demonstrates one method of using a wound covering to treat a patient with aggressive periodontitis. The wound covering was prepared according to the method of FIG. 2 and processed according to the methods described particularly in Example 1.

The patient was a 69 year old female who presented with a failing bridge from #29 tooth and #32 tooth due to localized severe chronic periodontal disease. Teeth #29 and #32 had a hopeless prognosis. The patient was missing teeth #30 and #31 and desired to replace teeth #29, #30 and #31 with dental implants. The patient had a buccal ridge deficiency in the #30 and #31 sites that would require bone grafting before implants could be placed.

Following extraction of tooth #29 and tooth #32, the mandibular ridge width in the #30-31 site was approximately 1-2 mm wide. Platelet-rich plasma and a liquid wound covering product were mixed and administered to the #29 and #32 sites to build bone in the #29, #30 and #31 sites. Two wound covering membranes (1.5 cm×2 cm each) were placed over the bone grafts before flap closure with sutures. FIGS. 9-12 indicate healing from 1-4 weeks post-surgery. It is noteworthy that the patient experienced little to no inflammation and swelling, as well as no pain at the surgical site. Postoperatively the surgical site exhibited excellent early soft tissue healing showing a 2 mm gain in clinical attachment and probing depth.

During the six month post-operative visit, the site was re-entered surgically. The ridge width in #30 and #31 site measured approximately 5 to 6 mm in width. Three dental implants were placed at this time in sites #29, #30, and #31. This case demonstrates that the wound covering is effective in the treatment and management of peridontitis.

EXAMPLE 3

The following example demonstrates one method of using a wound covering during medical treatment of a venous ulcer. The wound covering was prepared according to the method of FIG. 1.

Human birth tissue was obtained from a seronegative healthy mother via Cesarean section. To maximize the overall quality of the donated tissue, a recovery technician was present in the operating room during the donor's Cesarean section to assist the physician with recovery, treatment and handling of the birth tissue. The donor was surgically prepped and draped per AORN standards prior to the Cesarean section procedure. The recovery technician prepared the recovery site by establishing a sterile field on a back table in the operating room. Following delivery of the baby, the physician's assistant placed the human birth tissue en-bloc into a sterile basin. Maintaining sterility, the basin was transferred to the recovery technician onto the sterile field. Beginning at the amnion/chorion membrane surgical incision site, the recovery technician used blunt dissection to separate the chorionic membrane from the amniotic membrane, using care not to tear the amniotic tissue. The recovery technician then removed the amniotic membrane from the placental face until reaching the umbilical cord. At the site where the amnion is attached to the umbilical cord, the recovery technician dissected the amnion from the umbilical cord by making an incision in the amnion around the circumference of the umbilical cord. The amniotic membrane was transferred to a sterile container and rinsed with sterile saline to remove any blood or debris.

After thorough rinsing, the amniotic membrane was transferred into a sterile bag and swab cultures were performed. Approximately 300 ml of transport solution (15% NaCl) was added to the sterile bag containing the recovered amniotic membrane. The bag was secured with a knot. The single-bagged amniotic membrane was then placed into a second sterile bag, which was securely knotted. The double-bagged amniotic membrane was then transferred into a plastic transport container to which the appropriate identification was affixed. The plastic transport container was placed in a qualified shipping container with an appropriate amount of wet ice to maintain refrigerated temperatures. The validated box arrived at the processing facility within 2.5 hours following recovery and was immediately placed in refrigerated temperatures (1-10° C.) and inspected per standard operating procedures.

A sterile field was established in a validated cleanroom at the processing facility. All manufacturing steps were recorded concurrently by a circulating technician on a designated processing record. The amniotic membrane was removed from the plastic transport container and outer bag. The inner bag containing the amniotic membrane was aseptically passed onto a sterile field. The amniotic membrane was placed maternal side up on a sterile cutting board. The membrane was inspected for any damage or debris. Any stringy ends were cut away. Keeping the membrane flat on the sterile cutting board, the amnion was rinsed with a sterile saline solution (0.9% NaCl). The maternal side of the membrane was covered with sterile mesh, allowing the mesh to slightly overlap the membrane. The membrane was gently lifted, positioned fetal side up, and placed back onto the sterile cutting board, using caution to not disturb the mesh/amnion interface. The fetal side of the membrane was rinsed with a sterile saline solution (0.9% NaCl). Then, the fetal side of the membrane was covered with sterile mesh, allowing the mesh to slightly overlap the membrane. The mesh/membrane/mesh was transferred into a sterile basin, maternal side down, unfolded and flat, using caution not to disturb the mesh/amnion interface. 1 L of 95.5% ethanol solution was added to the sterile basin, fully immersing the mesh/membrane/mesh interface and the basin was re-covered. The sterile basin was placed inside a sterile bag and transferred to a quarantine refrigerator. The mesh/membrane/mesh interface remained in the 1 L of 95.5% ethanol solution for 24.1 hours.

A sterile field was established in a validated cleanroom at the processing facility. All manufacturing steps were recorded concurrently by a circulating technician on a designated processing record. The sterile bag containing the sterile basin was removed from the quarantine refrigerator. The sterile basin was removed from the sterile bag and aseptically transferred to the sterile work area in the cleanroom. The mesh/membrane/mesh interface was removed from the 95.5% ethanol solution and placed maternal side down on a sterile cutting board. The mesh was removed from the fetal side of the membrane. The membrane/mesh was carefully flipped, and the mesh was removed from the maternal side of the membrane. The membrane was repositioned onto the cutting board in a completely flat position. The membrane was allowed to dry for seven (7) minutes. Using a rotary cutting blade, the membrane was sectioned into product sizes, in accordance with the processing plan. The dry membrane grafts were carefully loosened from the cutting board and placed onto pre-cut sections of mesh with the maternal side of each membrane graft orienting up and the fetal side to the mesh. Each individual tissue patch was packaged into a sterile foil inner pouch using aseptic technique. Using an AccuSeal 540Plus sealer, each foil pouch was sealed inside a Tyvek pouch following standard operating procedures. Each Tyvek pouch was assigned and labeled with a tissue identification number, designed to ensure the traceability of tissue from receipt through clinical use, transfer or destruction. Each unit was terminally sterilized via E Beam irradiation at 26.8-28.6 kGy.

The patient was a 71-year-old man who presented with a venous ulcer of unknown origin on the area to the left ankle proximal and distal. The wound was diagnosed as a venous stasis ulcer of the left medial malleolus. Upon physical exam the patient had a 0.9 cm×0.7 cm wound with a depth of 0.1 cm. Patient had a history of smoking (1 pack per day), peripheral vascular disease, varicosity of the lower legs, and venous stasis with dermatoliposclerosis. After four weeks of treatment, the wound was not healing via traditional methods. Based on the patient history, physical exam and status of the wound, the patient was treated with a topical wound covering, prepared according to the method of FIG. 1.

The wound was debrided and the wound covering was placed over the wound with the edges secured with Steri-Strips. The wound and wound covering were then covered with a non-adherent dressing. Weekly follow-up visits were planned and the wound was monitored for healing and/or complications. Week 2 assessment noted that the wound covering had incorporated and the margins were closing. The wound measured 0.5 cm×0.2 cm with a depth of 0.1 cm. Week 6 assessment noted that the wound was closed with no complication.

EXAMPLE 4

The following example demonstrates one method of using wound coverings during medical treatment of a non-healing surgical wound. The wound coverings were prepared according to the method of FIG. 1. The first wound covering was processed according to the methods described particularly in Example 3. The second wound covering was processed substantially the same as the methods described in Example 3, with the exception of the following steps: (i) the mesh/membrane/mesh interface remained in the 1 L of 95.5% ethanol solution for 148 hours; (ii) the membrane was allowed to dry for fifteen minutes; and (iii) the unit was terminally sterilized via E Beam irradiation at 28.0-29.9 kGy.

Figure 13:
FIG. 13 provides a photo of a surgical wound prior to treatment with a wound covering according to one embodiment.

The patient was a 92-year-old woman who presented with a surgical wound sustained via surgical removal of a basal cell carcinoma on her lower left extremity. Upon physical exam, the patient had a 7.5 cm×5 cm wound with a depth of 0.5 cm (FIG. 13).The patient had a history of lung cancer, peripheral arterial occlusive disease (PAOD), osteoarthritis, diabetes and basal cell carcinoma. The basal cell carcinoma was removed and traditional wound care efforts were instituted. At 6 weeks post-op, the wound was not healing via traditional methods. Based on the patient history, physical exam, and status of the wound, the patient was treated with two topical wound coverings, prepared according to the methods described above.

Figure 14:
FIG. 14 provides a photo of the surgical wound of FIG. 13 upon placement of a wound covering according to one embodiment.
Figure 15:
FIG. 15 provides a photo of the surgical wound of FIG. 13 one week after treatment with a wound covering according to one embodiment.
Figure 16:
FIG. 16 provides a photo of the surgical wound of FIG. 13 eight weeks after treatment with a wound covering according to one embodiment.

The wound was debrided and the wound covering was placed over the wound with the edges secured with Steri-Strips (FIG. 14). The wound and wound covering were then covered with a non-adherent dressing. Weekly follow-up visits were planned and the wound was monitored for healing and/or complications. Week 1 assessment noted that the wound covering had incorporated and the margins were closing (FIG. 15). Week 8 assessment noted that the wound was nearly closed with a small segment of the wound left and progressing to closure (2 cm×1.5 cm, 1 mm depth) (FIG. 16). Patient was phoned for a follow-up visit at week 12 and stated that the wound had completely closed, and she would not be returning for follow-up.

EXAMPLE 5

The following example demonstrates one method of using a wound covering during medical treatment of a trauma wound. The wound covering was prepared according to the method of FIG. 1 and processed according to the methods described in Example 3.

The patient was an 85-year-old woman who presented with a traumatic wound sustained to the right lateral leg via accidental skin tear with a wheelchair which became infected. The patient was treated for infection which resolved in two weeks, but the wound had not healed. Upon physical exam the patient had a 4 cm length×2.5 cm width× 0.2 cm depth. Patient had a history of congestive heart failure, hyperlipidemia, hypertension, venous insufficiency—history of cellulitis, gastroesophageal reflux, kidney stones, anemia, rheumatoid arthritis, dementia, and a history of transient ischemic attacks. At six weeks after the injury, the wound was not healing via traditional methods. Based on the patient history, physical exam and status of the wound, the patient was treated with a topical wound covering, prepared according to the method of FIG. 1.

The wound was debrided and the wound covering was placed over the wound with edges secured with Steri-Strips. The wound and wound covering were then covered with a non-adherent dressing. Weekly follow-up visits were planned and the wound was monitored for healing and/or complications.

Week 3 assessment noted that the wound covering had incorporated with wound margins of 2 cm length×1.2 cm width×0 cm depth. Week 7 assessment noted that the wound margins were 0.5 cm length×0.4 cm width×0 cm depth. Week 12 assessment noted that the wound was completely closed with no associated complications.

EXAMPLE 6

The following example demonstrates one method of using a wound covering during medical treatment of a diabetic ulcer. The wound covering was prepared according to the method of FIG. 1 and processed substantially the same as the methods described in Example 3, with the exception of the following step: the mesh/membrane/mesh interface remained in the 1 L of 95.5% ethanol solution for 26.5 hours.

The patient was a 53-year-old woman who presented with a diabetic ulcer secondary to severe cellulitis with recent culture of group B *streptococcus* and methicillin-resistant *staphylococcus aureus* (MRSA). The wound was diagnosed as a chronic complicated left heel ulcer. Upon physical exam the patient had a 0.7 cm×0.5 cm wound with a depth of 0.2 cm. The patient had a history of peripheral vascular disease, diabetes, cataracts, peripheral neuropathy and stent placement. After 45 weeks of treatment, the wound was not healing via traditional methods. Based on the patient history, physical exam and status of the wound, the patient was treated with a topical wound covering, prepared according to the method of FIG. 1.

The wound was debrided and the wound covering was placed over the wound with edges secured with Steri-Strips. The wound and wound covering were then covered with a non-adherent dressing. Weekly follow-up visits were planned and the wound was monitored for healing and/or complications.

Week 4 assessment noted that the wound covering had incorporated and the margins were closing. At week 4, the wound measured 0.3 cm×0.4 cm, with a depth of 0.2 cm. Week 6 assessment noted that the wound was closed with no complication.

EXAMPLE 7

Representative samples of final product from four production lots #1, #2, #3 and #4 manufactured according to the methods of FIG. 2 were tested for residual glutaraldehyde and residual ethanol by gas chromatography, analytical methods EPA 8015M, CAS No. 111-30-8 and EPA 8260B, CAS No. 64-17-5, respectively. Samples were sent to Nelson Laboratories, Inc., 6280 South Redwood Road Salt Lake City, Utah 84123, a GLP qualified microbiology laboratory registered with the FDA and third-party accredited to ISO 17025 standards. The results are summarized in Table 1 and Table 2 below.

Samples from four production lots #1, #2, #3 and #4 were tested for residual glutaraldehyde by gas chromatography, analytical methods EPA 8015M, CAS No. 111-30-8 as follows:

Three representative samples of final product (2 cm×2 cm each) from production lot #1 included amniotic membranes that had been treated with a 0.1% glutaraldehyde composition for a period of 15 minutes and had been immersed in an alcohol composition comprising 95.5% ethanol for a period of 24 hours.

Zero headspace extraction was performed with double deionized water as the vehicle extractant. Extraction vessels were tumbled during the entire extraction process. For production lot #1, the three samples were pooled, and a test article was extracted with a weight of 0.046 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #1.

One sample of final product (4 cm×4 cm) from production lot #2 included an amniotic membrane that had been treated with a 0.1% glutaraldehyde composition for a period of 15 minutes and had been immersed in an alcohol composition comprising 95.5% ethanol for a period of 24.1 hours.

Zero headspace extraction was performed with double deionized water as the vehicle extractant. Extraction vessels were tumbled during the entire extraction process. For production lot #2, one test article was extracted with a weight of 0.051 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #2.

Two representative samples of final product (2 cm×6 cm each) from production lot #3 included amniotic membranes that had been treated with a 0.1% glutaraldehyde composition for a period of 15 minutes and had been immersed in an alcohol composition comprising 95.5% ethanol for a period of 41.3 hours.

Zero headspace extraction was performed with double deionized water as the vehicle extractant. Extraction vessels were tumbled during the entire extraction process. For production lot #3, the two samples were pooled, and a test article was extracted with a weight of 0.069 g and a fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #3.

One sample of final product (4 cm×4 cm) from production lot #4 included an amniotic membrane that had been treated with a 0.1% glutaraldehyde composition for a period of 15 minutes and had been immersed in an alcohol composition comprising 95.5% ethanol for a period of 114.7 hours.

Zero headspace extraction was performed with double deionized water as the vehicle extractant. Extraction vessels were tumbled during the entire extraction process. For production lot #4, one test article was extracted with a weight of 0.037 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was analyzed by gas chromatography for glutaraldehyde determination. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No glutaraldehyde was detected at the reported detection limit (1.0 mg/L) for production lot #4.

Samples from the same four production lots #1, #2, #3 and #4 were tested for residual ethanol by gas chromatography, analytical methods EPA 8260B, CAS No. 64-17-5, as follows:

Three representative samples of final product (2 cm×2 cm each) from production lot #1 included amniotic membranes that had been treated with a 0.1% glutaraldehyde composition for a period of 15 minutes and had been immersed in an alcohol composition comprising 95.5% ethanol for a period of 24 hours.

Zero headspace extraction was performed with double deionized water as the vehicle extractant. Extraction vessels were tumbled during the entire extraction process. For production lot #1, the three samples were pooled, and a test article was extracted with a weight of 0.05 g and fluid amount of 100 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #1.

One sample of final product (4 cm×4 cm) from production lot #2 included an amniotic membrane that had been treated with a 0.1% glutaraldehyde composition for a period of 15 minutes and had been immersed in an alcohol composition comprising 95.5% ethanol for a period of 24.1 hours.

Zero headspace extraction was performed with double deionized water as the vehicle extractant. Extraction vessels were tumbled during the entire extraction process. For production lot #2, one test article was extracted with a weight of 0.04 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #2.

Two samples of final product (4 cm×4 cm and 2 cm×6 cm) from production lot #3 included amniotic membranes that had been treated with a 0.1% glutaraldehyde composition for a period of 15 minutes and had been immersed in an alcohol composition comprising 95.5% ethanol for a period of 41.3 hours.

Zero headspace extraction was performed with double deionized water as the vehicle extractant. Extraction vessels were tumbled during the entire extraction process. For production lot #3, the two samples were pooled, and a test article was extracted with a weight of 0.08 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #3.

Two samples of final product (4 cm×4 cm each) from production lot #4 included amniotic membranes that had been treated with a 0.1% glutaraldehyde composition for a period of 15 minutes and had been immersed in an alcohol composition comprising 95.5% ethanol for a period of 114.7 hours.

Zero headspace extraction was performed with double deionized water as the vehicle extractant. Extraction vessels were tumbled during the entire extraction process. For production lot #4, the two samples were pooled, and a test article was extracted with a weight of 0.09 g and fluid amount of 50 ml. The starting extraction temperature was 22° C. and the ending extraction temperature was 23° C. The extraction lasted twenty-four hours.

All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis, Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

No ethanol was detected at the reported detection limit (0.5 mg/L) for production lot #4.

TABLE 1

Glutaraldehyde Determination for Production Lots

| Production Lot | Total Time in Glutaraldehyde | Weight of Sample | Volume of Fluid | Starting Extraction Temperature | Ending Extraction Temperature | Duration of Extraction | Sample Results |
|---|---|---|---|---|---|---|---|
| 1 | 15 Minutes | 0.046 g | 100 mL | 22° C. | 23° C. | 24 Hours | ND* |
| 2 | 15 Minutes | 0.051 g | 100 mL | 22° C. | 23° C. | 24 Hours | ND* |
| 3 | 15 Minutes | 0.069 g | 100 mL | 22° C. | 23° C. | 24 Hours | ND* |
| 4 | 15 Minutes | 0.037 g | 100 mL | 22° C. | 23° C. | 24 Hours | ND* |

*ND = Not Detected at the Minimum Reporting Limit (1.0 mg/L)

TABLE 2

Ethanol Determination for Production Lots

| Production Lot | Total Time in Ethanol | Weight of Sample | Volume of Fluid | Starting Extraction Temperature | Ending Extraction Temperature | Duration of Extraction | Sample Results |
|---|---|---|---|---|---|---|---|
| 1 | 24.0 Hours | 0.05 g | 50 mL | 22° C. | 23° C. | 24 Hours | ND* |
| 2 | 24.1 Hours | 0.04 g | 50 mL | 22° C. | 23° C. | 24 Hours | ND* |
| 3 | 41.3 Hours | 0.08 g | 50 mL | 22° C. | 23° C. | 24 Hours | ND* |
| 4 | 114.7 Hours | 0.09 g | 50 mL | 22° C. | 23° C. | 24 Hours | ND* |

*ND = Not Detected at the Minimum Reporting Limit (0.5 mg/L)

EXAMPLE 8

Three representative samples of final product for each of three production lots manufactured according to the methods of FIG. 1 were tested for residual ethanol by gas chromatography, analytical method EPA 8260B, CAS No. 64-17-5. Samples were sent to Nelson Laboratories, Inc., 6280 South Redwood Road Salt Lake City, Utah 84123, a GLP qualified microbiology laboratory registered with the FDA and third-party accredited to ISO 17025 standards.

The three samples submitted for testing from production lot #5 (2 cm×3 cm; 2 cm×3 cm; and 1.5 cm×2 cm) included amniotic membranes that had been immersed in an alcohol composition comprising 95.5% ethanol for a period of 110 hours. The three samples submitted for testing from production lot #6 (2 cm×3 cm each) included amniotic membranes that had been immersed in an alcohol composition comprising 95.5% ethanol for a period of 25.5 hours. The three samples submitted for testing from production lot #7 (2 cm×3 cm each) included amniotic membranes that had been immersed in an alcohol composition comprising 95.5% ethanol for a period of 24.9 hours.

Zero headspace extraction was performed with double deionized water as the vehicle extractant. Extraction vessels were tumbled during the entire extraction process. For each of the three production lots, the samples were pooled, and one test article was extracted with a weight of 0.05 g and fluid amount of 50 ml. The starting extraction temperature was 22° C. and the ending extraction temperature was 23° C. The extractions lasted twenty-four hours. All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography-mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

The certificates of analyses for production lots #5, #6 and #7 indicated no detectable amounts of ethanol at the minimum reporting limit (0.5 mg/L). The results are summarized in Table 3 below.

TABLE 3

Ethanol Determination for Production Lots

| Production Lot | Total Time in Ethanol | Weight of Sample | Volume of Fluid | Starting Extraction Temperature | Ending Extraction Temperature | Duration of Extraction | Sample Results |
|---|---|---|---|---|---|---|---|
| 5 | 110.0 Hours | 0.05 g | 50 mL | 22° C. | 23° C. | 24 Hours | ND* |

TABLE 3-continued

Ethanol Determination for Production Lots

| Production Lot | Total Time in Ethanol | Weight of Sample | Volume of Fluid | Starting Extraction Temperature | Ending Extraction Temperature | Duration of Extraction | Sample Results |
|---|---|---|---|---|---|---|---|
| 6 | 25.5 Hours | 0.05 g | 50 mL | 22° C. | 23° C. | 24 Hours | ND* |
| 7 | 24.9 Hours | 0.05 g | 50 mL | 22° C. | 23° C. | 24 Hours | ND* |

*ND = Not Detected at the Minimum Reporting Limit (0.5 mg/L)

I claim:

1. A resorbable wound covering comprising,
at least one chemically dehydrated, cross-linked amniotic membrane,
made by a method wherein an amniotic membrane is recovered from a human and is immersed in an about 0.1% glutaraldehyde cross-linking solution for about 15 minutes to form a cross-linked amniotic membrane,
wherein the cross-linked membrane is treated with a single alcohol composition for about 24 hours to about 384 hours to chemically dehydrate the cross-linked membrane followed by terminal sterilization to form the resorbable wound covering, and
wherein the alcohol composition comprises from about 90% to about 99% ethanol.

2. The resorbable wound covering of claim 1, wherein the cross-linked membrane is rinsed in a sterile saline solution after immersion in the 0.1% glutaraldehyde cross-linking solution.

3. The resorbable wound covering of claim 1, wherein terminal sterilization is gamma irradiation or electron beam irradiation.

4. The resorbable wound covering of claim 1, wherein the resorbable wound covering is about 0.02 mm to about 0.35 mm thick.

5. The resorbable wound covering of claim 1, wherein the resorbable wound covering is held at a wound site by a patient's musculature, skin, or a combination thereof.

6. A method of treating a wound comprising the steps of:
preparing a resorbable wound covering according to claim 1; and
placing the wound covering on or around a wound.

7. The method of claim 6, further comprising the step of hydrating the resorbable wound covering at an application site.

8. The method of claim 6, further comprising the step of securing the resorbable wound covering on or around the wound.

9. The method of claim 6, wherein the resorbable wound covering is employed for adhesion prevention post-surgery.

10. The method of claim 6, wherein the wound is the result of a non-healing surgical site.

11. The method of claim 6, wherein the wound is in or around an existing or extracted tooth.

12. The method of claim 6, wherein the wound comprises a skin tear, diabetic ulcer, decubitus ulcer, venous leg ulcer, arterial leg ulcer, cutaneous ulcer, or a wound arising on or around a soft tissue, nerve, organ, vascular tissue, muscle, spinal cord, bone, oral cavity, ocular surface, or a combination thereof.

* * * * *